United States Patent
Stone

(10) Patent No.: US 7,621,961 B2
(45) Date of Patent: Nov. 24, 2009

(54) SHOULDER IMPLANT ASSEMBLY

(75) Inventor: Kevin T Stone, Winona Lake, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 0 days.

(21) Appl. No.: 11/705,329

(22) Filed: Feb. 12, 2007

(65) Prior Publication Data

US 2007/0142918 A1 Jun. 21, 2007

Related U.S. Application Data

(62) Division of application No. 10/680,924, filed on Oct. 8, 2003, now Pat. No. 7,175,663.

(51) Int. Cl.
*A61F 2/40* (2006.01)

(52) U.S. Cl. .................. 623/19.12; 623/19.13

(58) Field of Classification Search ... 623/19.11–19.14, 623/17.11–17.16
See application file for complete search history.

(56) References Cited

U.S. PATENT DOCUMENTS

| | | | |
|---|---|---|---|
| 3,815,157 A | 6/1974 | Skorecki et al. |
| 3,842,442 A | 10/1974 | Kolbel |
| 3,916,451 A | 11/1975 | Buechel et al. |
| 3,978,528 A | 9/1976 | Crep |
| 3,979,778 A | 9/1976 | Stroot |
| 4,003,095 A | 1/1977 | Gristina |
| 4,030,143 A | 6/1977 | Elloy et al. |
| 4,040,131 A | 8/1977 | Gristina |
| 4,135,517 A | 1/1979 | Reale |
| 4,179,758 A | 12/1979 | Gristina |
| 4,206,517 A | 6/1980 | Pappas et al. |
| 4,693,723 A | 9/1987 | Gabard |
| 4,822,370 A | 4/1989 | Schelhas |
| 4,865,605 A | 9/1989 | Dines et al. |
| 4,865,609 A | 9/1989 | Roche |
| 4,919,670 A | 4/1990 | Dale et al. |
| 4,957,510 A | 9/1990 | Cremascoli |
| 4,963,155 A | 10/1990 | Lazzeri et al. |
| 5,080,673 A | 1/1992 | Burkhead et al. |
| 5,080,685 A | 1/1992 | Bolesky et al. |
| 5,135,529 A | 8/1992 | Paxson et al. |
| 5,181,928 A | 1/1993 | Bolesky et al. |
| 5,201,882 A | 4/1993 | Paxson |
| 5,222,984 A | 6/1993 | Forte |
| 5,314,479 A | 5/1994 | Rockwood, Jr. et al. |
| 5,358,526 A | 10/1994 | Tornier |

(Continued)

FOREIGN PATENT DOCUMENTS

DE 19509037 9/1996

(Continued)

OTHER PUBLICATIONS

"Buechel-Pappas™ Total Shoulder System," Endotec, Jul. 1991.

(Continued)

*Primary Examiner*—Bruce E Snow
(74) *Attorney, Agent, or Firm*—Harness, Dickey

(57) ABSTRACT

An implant assembly and associated method for selectively performing reverse and traditional arthroplasty for a shoulder joint that includes a humerus and a glenoid. The implant assembly may include a head, a cup, a humeral stem and an adapter. The method includes inserting the humeral stem to the humerus and connecting a male taper of the adapter to a female taper of the head. For reverse arthroplasty, the method includes attaching the adapter to the glenoid and the cup to the stem. For traditional arthroplasty, the method includes attaching the adapter to the humeral stem and the cup to the glenoid. The method also includes articulating the head with the cup.

7 Claims, 11 Drawing Sheets

| | | | | | | |
|---|---|---|---|---|---|---|
| 5,462,563 | A | 10/1995 | Shearer et al. | 2004/0064190 A1 | 4/2004 | Ball et al. |
| 5,507,817 | A | 4/1996 | Craig et al. | 2004/0220673 A1 | 11/2004 | Pria |
| 5,507,824 | A | 4/1996 | Lennox | 2004/0220674 A1 | 11/2004 | Pria |
| 5,549,682 | A | 8/1996 | Roy | | | |
| 5,580,352 | A | 12/1996 | Sekel | | | |

FOREIGN PATENT DOCUMENTS

| | | |
|---|---|---|
| EP | 0 257 359 | 3/1988 |
| EP | 0 599 429 | 6/1994 |
| EP | 0 664 108 | 7/1995 |
| EP | 0 679 375 | 11/1995 |
| EP | 0 797 964 | 10/1997 |
| EP | 0 712 617 | 12/1997 |
| EP | 1472999 | 11/2004 |
| EP | 1520560 | 4/2005 |
| EP | 1539965 | 3/2006 |
| FR | 2 574 283 | 6/1986 |
| FR | 2 652 298 | 4/1991 |
| FR | 2 652 498 | 4/1991 |
| FR | 2 664 809 | 1/1992 |
| FR | 2704747 | 11/1994 |
| FR | 2 721 200 | 12/1995 |
| FR | 2848099 | 6/2004 |
| FR | 2852229 | 9/2004 |
| GB | 2405346 | 3/2005 |
| WO | WO 95/22302 | 8/1995 |
| WO | WO 96/22302 | 8/1995 |
| WO | WO-9522302 | 8/1995 |
| WO | WO 96/17553 | 6/1996 |
| WO | WO 98/46172 | 10/1998 |
| WO | WO 00/15154 | 3/2000 |

| | | | |
|---|---|---|---|
| 5,702,457 | A | 12/1997 | Walch et al. |
| 5,702,486 | A | 12/1997 | Craig et al. |
| 5,723,018 | A | 3/1998 | Cyprien et al. |
| 5,728,161 | A | 3/1998 | Camino et al. |
| 5,902,340 | A | 5/1999 | White et al. |
| 5,910,171 | A | 6/1999 | Kummer et al. |
| 5,961,555 | A | 10/1999 | Huebner |
| 6,033,439 | A | 3/2000 | Camino et al. |
| 6,045,582 | A | 4/2000 | Prybyla |
| 6,102,953 | A | 8/2000 | Huebner |
| 6,129,764 | A | 10/2000 | Servidio |
| 6,171,341 | B1 | 1/2001 | Boileau et al. |
| 6,197,062 | B1 | 3/2001 | Fenlin |
| 6,197,063 | B1 | 3/2001 | Dews |
| 6,206,925 | B1 | 3/2001 | Tornier |
| 6,228,120 | B1 | 5/2001 | Leonard et al. |
| 6,364,910 | B1 | 4/2002 | Shultz et al. |
| 6,368,352 | B1 | 4/2002 | Camino et al. |
| 6,620,197 | B2 | 9/2003 | Maroney et al. |
| 6,626,946 | B1 | 9/2003 | Walch et al. |
| 6,719,799 | B1 | 4/2004 | Kropf et al. |
| 6,761,740 | B2 | 7/2004 | Tornier |
| 6,790,234 | B1 | 9/2004 | Frankle |
| 6,942,699 | B2 | 9/2005 | Stone et al. |
| 6,974,483 | B2 | 12/2005 | Murray |
| 6,986,790 | B2 | 1/2006 | Ball et al. |
| 7,097,663 | B1 | 8/2006 | Nicol et al. |
| 7,135,044 | B2 | 11/2006 | Bassik et al. |
| 7,175,663 | B1 | 2/2007 | Stone |
| 2001/0049561 | A1 | 12/2001 | Dews et al. |
| 2001/0053935 | A1 | 12/2001 | Hartdegen et al. |
| 2002/0120339 | A1 | 8/2002 | Callaway et al. |
| 2002/0138148 | A1 | 9/2002 | Hyde, Jr. |
| 2003/0097183 | A1 | 5/2003 | Rauscher et al. |
| 2003/0114933 | A1 | 6/2003 | Bouttens et al. |
| 2003/0158605 | A1 | 8/2003 | Tornier |
| 2004/0064189 | A1 | 4/2004 | Maroney et al. |

OTHER PUBLICATIONS

"Delta Prothese Totale D'epaule Inversee", Depuy (8 sheets).
"Reverse Shoulder Prosthesis", Encore Surgical (2 sheets).
"Surgery Eases Rotator Cuff Pain" by Ruth Campbell Odessa American, online article, (2 sheets) dated Feb. 9, 2005.
Thabe, et al., "Die endoprothetische Versorgung des rheumatischen Schultergelenkes," Aktuelle Rheumatologie, vol. 19 (1994), pp. 155-160 (with English Abstract).
Thabe, et al., "Modulares—Vario—Schulter," 6 sheets of pictures.
The Delta CTA™ Reverse Shoulder System, copyright Johnson & Johnson Gateway LLC 2000-20005 online article (2 sheets) dated Feb. 9, 2005.

SHOULDER IMPLANT ASSEMBLY

CROSS-REFERENCE TO RELATED APPLICATIONS

This application is a divisional application of U.S. patent application Ser. No. 10/680,924, filed on Oct. 8, 2003 (now U.S. Pat. No. 7,175,663, issued Feb. 13, 2007). The disclosure of the above application is incorporated herein by reference.

FIELD OF THE INVENTION

The present invention relates to an implant assembly for shoulder joint replacement.

BACKGROUND OF THE INVENTION

A natural shoulder joint may undergo degenerative changes caused by a variety of reasons. When these degenerative changes become so far advanced and irreversible, it may ultimately become necessary to replace a natural shoulder joint with a prosthetic shoulder joint. In the traditional implantation of a shoulder joint prosthesis, the natural head portion of the humerus is resected and a cavity is created in the intramedullary canal of the host humerus for accepting a humeral component. The humeral component generally includes a stem, and a head portion, which is used to replace the natural head of the humerus. Once the humeral component has been implanted, the glenoid cavity positioned at the scapula may also be resected and shaped to accept a glenoid component. The glenoid component generally includes an articulating surface or cup which is engaged by the head portion of the humeral component. Modular designs for the humeral and glenoid components are currently available for the traditional shoulder arthroplasty, and components of different sizes or shapes are at the disposal of the surgeon performing the operation.

The traditional shoulder joint implantation requires that the rotator cuff muscles be present and functioning normally. When this is not the case, a reverse shoulder prosthesis may be preferable. In the reverse shoulder prosthesis, the humeral component includes a stem, and a cup connected to the stem. The glenoid component supports a head which articulates with the cup.

It is not always practical to determine well in advance of the procedure whether a reverse or traditional shoulder prosthesis should be used. It is, therefore, desirable to provide a selection of modular components that can be combined for use in traditional as well as reverse shoulder arthroplasty, with the goals of increasing flexibility and choice and for providing interchangeable and easy to use components that are also cost effective.

SUMMARY OF THE INVENTION

One embodiment of the invention provides an implant assembly for a shoulder joint that has a humerus and a glenoid. The implant assembly may include a humeral stem configured to be inserted in the humerus, and a head bounded by a convex surface and a planar base that has a female taper. The implant assembly also includes an adapter having a tray and an male taper. The tray may be configured to be attached to the glenoid. The male taper of the adapter is configured to be received in the female taper of the head. The implant assembly also includes a cup that can be attached to the stem. The cup has a concave surface that is configured to articulate with the convex surface of the head.

Another embodiment of the invention provides an assembly of implant components for a shoulder joint having a humerus and a glenoid. The assembly includes a humeral stem, a head having a convex surface, and a cup configured to articulate with the convex surface of the head. The assembly includes a glenoid adapter for a reverse shoulder arthroplasty, and a humeral adapter for traditional shoulder arthroplasty. The glenoid adapter is configured to connect the head to the glenoid when the cup is connected to the humeral stem. The humeral adapter is configured to connect the head to the humeral stem when the cup is connected to the glenoid. The same adapter may be used as a glenoid and as a humeral adapter.

Another embodiment of the invention provides an assembly of implant components for a shoulder joint having a humerus and a glenoid. The assembly includes a plurality of humeral stems, a plurality of heads, and a plurality of cups configured to articulate with the heads. The assembly also includes a plurality of glenoid adapters for a reverse shoulder arthroplasty, and a plurality of humeral adapters for traditional shoulder arthroplasty. Each glenoid adapter is configured to connect one of the heads to the glenoid when one of the cups is connected to one of the humeral stems. Each humeral adapter is configured to connect one of the heads to one of the humeral stems when one of the cups is connected to the glenoid.

Another embodiment provides a method for selectively performing reverse and traditional arthroplasty for a shoulder joint that includes a humerus and a glenoid. The method includes providing a head, a cup, and a humeral stem. The method also includes providing a humeral adapter for traditional arthroplasty, and providing a glenoid adapter for reverse arthroplasty. Further, the method includes selecting one of the humeral and glenoid adapters, and performing the corresponding arthroplasty utilizing the head, the cup, the humeral stem and the selected adapter.

Another embodiment provides a method for selectively performing reverse and traditional arthroplasty for a shoulder joint that includes a humerus and a glenoid. The method includes inserting a humeral stem to the humerus and connecting an adapter to a head with mating male and female tapers. The method also includes selectively attaching a base of the adapter to the glenoid for reverse arthroplasty, and to the stem for traditional arthroplasty, and selectively attaching a cup to the stem for reverse arthroplasty, and to the glenoid for traditional arthroplasty. Further, the method includes articulating the head with the cup.

Further areas of applicability of the present invention will become apparent from the detailed description provided hereinafter. It should be understood that the detailed description and specific examples, while indicating current embodiments of the invention, are intended for purposes of illustration only and are not intended to limit the scope of the invention.

BRIEF DESCRIPTION OF THE DRAWINGS

The present invention will become more fully understood from the detailed description and the accompanying drawings. The components in the drawings are not necessarily to scale, emphasis instead being placed upon illustrating the principles of the invention.

DETAILED DESCRIPTION OF THE PREFERRED EMBODIMENTS

The following description of the preferred embodiments of the invention is merely exemplary in nature and is in no way intended to limit the invention, its application, or uses.

Figure 1:
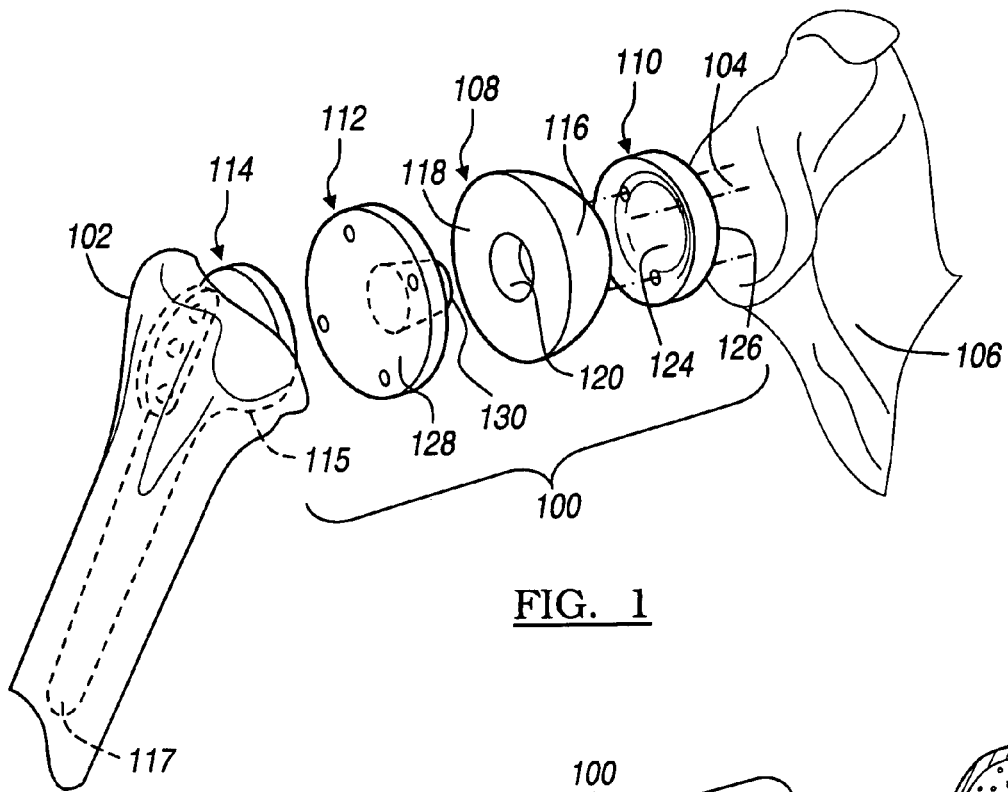
FIG. 1 is an exploded view of an embodiment of an implant assembly according to the invention, shown in a traditional shoulder arthroplasty.
Figure 2:
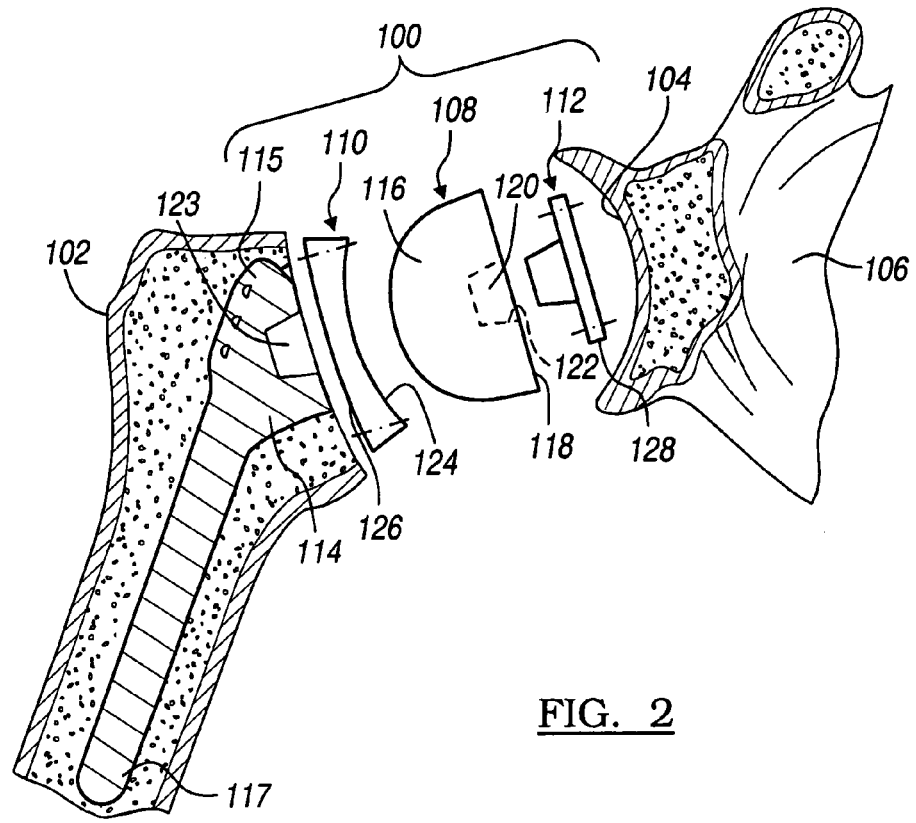
FIG. 2 is an exploded view of an embodiment of an implant assembly according to the invention, shown in a reverse shoulder arthroplasty.

Referring to FIGS. 1 and 2, there is shown an embodiment of an implant assembly 100 for a total shoulder joint replacement. The implant assembly 100 is configured to be implanted between a resected humerus 102 and a glenoid cavity ("glenoid") 104 of a scapula 106 in one of two ways, i.e., in a traditional arthroplasty depicted in FIG. 1, or in a reverse arthroplasty depicted in FIG. 2, by selecting and/or reconfiguring appropriately the components of the implant assembly 100. The implant assembly 100 includes a head 108, a cup 110, and an adapter 112. The implant assembly 100 may also include a humeral stem 114 that has a proximal end 115 and a distal end 117.

Figure 4A:
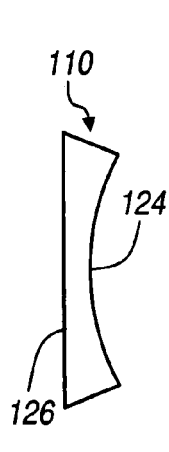
FIGS. 4a-4e are side views of embodiments of a cup according to the present invention.
Figure 4B:
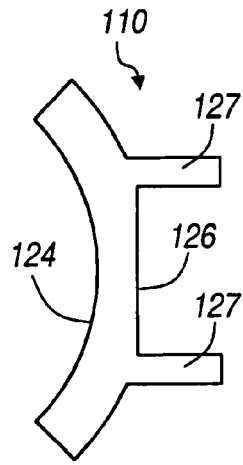
Figure 4C:
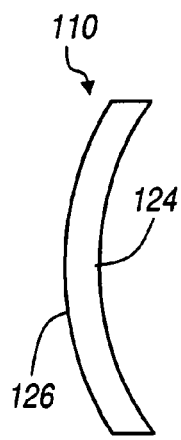
Figure 4D:
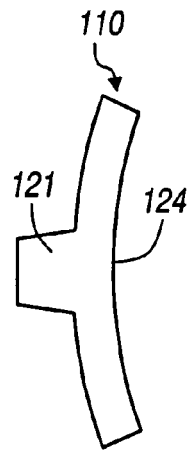
Figure 4E:
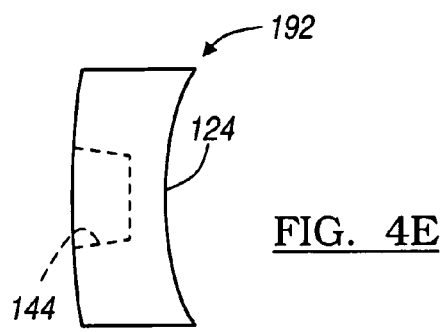
Figure 5A:
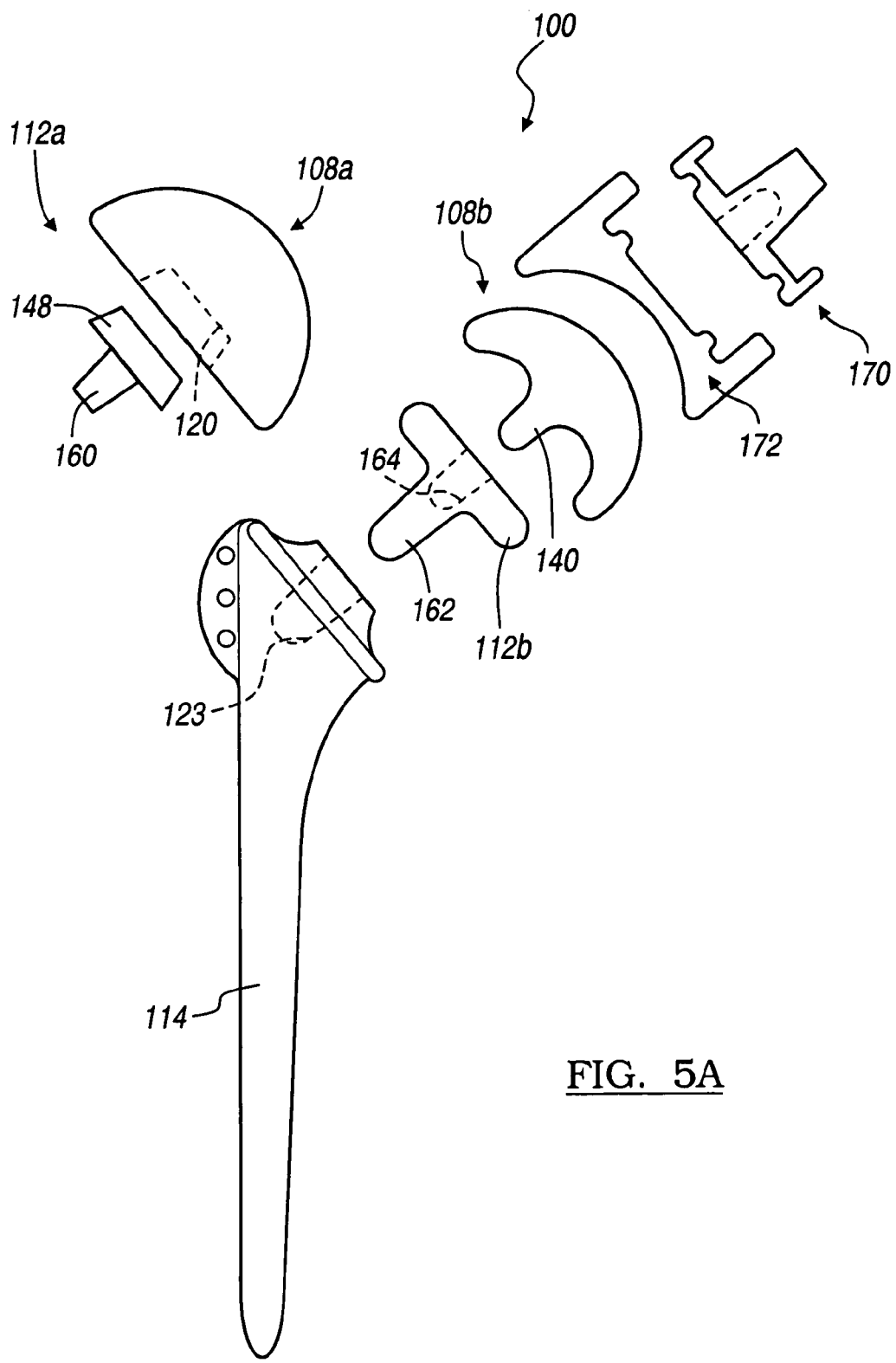
FIG. 5a is an exploded view of an embodiment of an implant assembly according to the invention, shown in a traditional shoulder arthroplasty and with alternative heads and humeral adapters.
Figure 15:
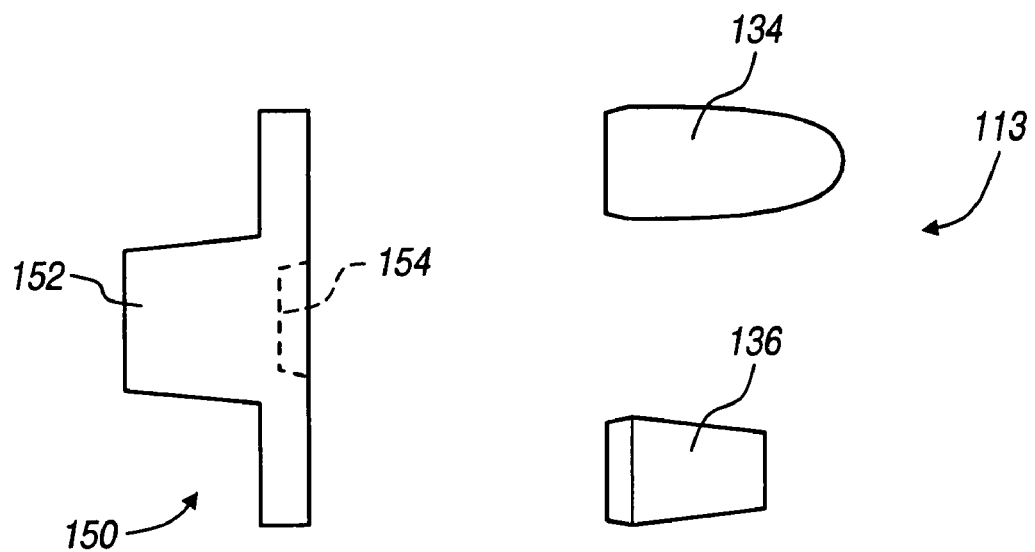
FIG. 15 is an exploded view of an embodiment of modular adapter, shown with glenoid and humeral stems.
Figure 16:
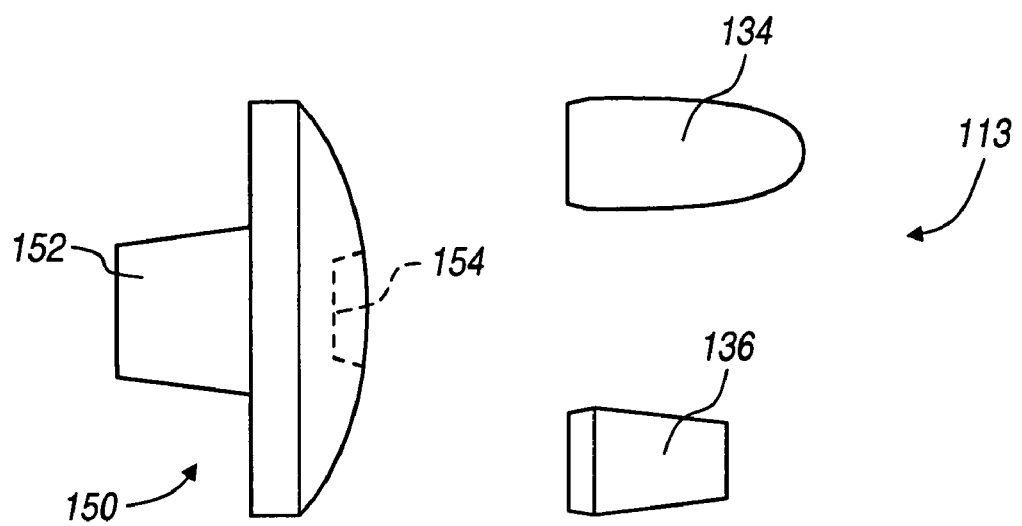
FIG. 16 is an exploded view of an embodiment of modular adapter; shown with glenoid and humeral stems.

Other embodiments of the implant assembly are shown in FIGS. 5a, 6a, 12, 13 for traditional shoulder replacement, and in FIGS. 5b, 6b, 7 and 14 for reverse shoulder replacement. FIGS. 3a-3d, 4a-4e, 9a-9c, 10a-10c, 11a-11c show representative embodiments of various components. FIGS. 15 and 16 show embodiments of a modular adapter 113. FIG. 8 shows an embodiment of a component assembly (kit) for shoulder replacement 800 showing different sizes of representative components. It should be understood that the component assembly 800 in FIG. 8 is only illustrative of the inclusion of different sizes of each component and it is not limited by the type of components actually shown. For example, the component assembly 800 may include different sizes of each of the heads 108 shown in FIGS. 9a-9c, different types and sizes of adapters 112, different sizes and types of cups 110, etc. Like reference numerals refer to like components. When clarity requires to differentiate between different embodiments of the same component, an alphabetic character is attached to the reference numeral. For example, the head 108 is referenced as head 108a and head 108b to distinguish between two different head embodiments, as shown in FIG. 5a.

Figure 9A:
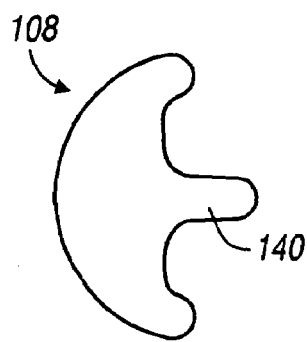
FIGS. 9a-9c are side views of embodiments of heads according to the invention.
Figure 9B:
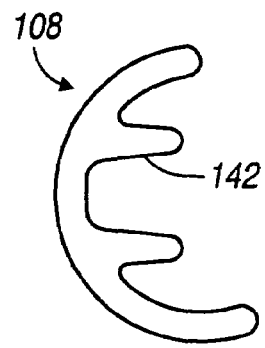
Figure 9C:
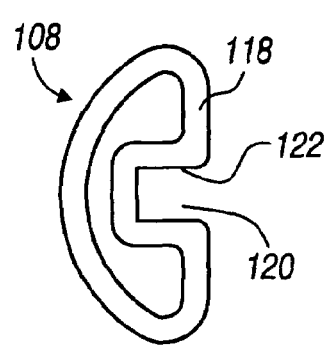
Figure 10A:
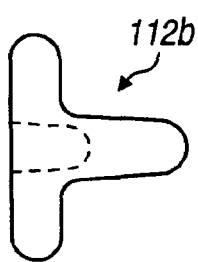
FIGS. 10a-10c are side views of embodiments of adapters corresponding to the heads of FIGS. 9a-9c.
Figure 10B:
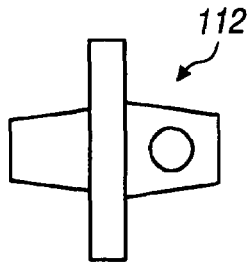
Figure 10C:
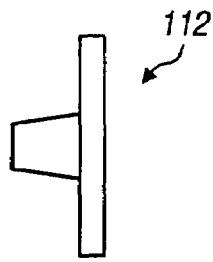

In the embodiment shown in FIGS. 1 and 2, the head 108 is bounded by a convex surface 116, which may be, for example, a hemispherical surface, and a base 118, which may be a substantially planar surface. In one embodiment, the base 118 may be modularly connected to the head 108. A female taper 120 with tapered inner walls 122 extends from the base 118 into the head 108. The convex surface 116 of the head 108 is shaped to articulate with a concave surface 124 of the cup 110 to allow for shoulder joint movement. Such articulation may be centered or eccentric. This and other embodiments of the head 108 are shown in FIGS. 9a-9c. In the embodiment of FIG. 9a, the head 108 has a male taper 140. In the embodiment of FIG. 9b, the head 108 has a female taper 142.

Referring to FIGS. 1 and 2, the cup 110 may include a back surface 126 that may be configured to be selectively attached to the humeral stem 114 in reverse shoulder arthroplasty, or to the resected glenoid 104 in the traditional shoulder arthroplasty. Alternatively, the cup 110 may be chosen from a number for available cups, such as those shown in FIGS. 4a-4d, some of which are better suited to either reverse shoulder arthroplasty or traditional shoulder arthroplasty. For example, the back surface 126 of the cup 110 may be a substantially planar surface which can be attached with cement or with mechanical fasteners, such as screws, to the humeral stem 114 or to the appropriately resected glenoid 104. Alternatively, as shown in FIG. 4c, the back surface 126 may be slightly convex. In the embodiment shown in FIG. 4b, the back surface 126 may include a number of pegs 127 for attachment to the glenoid 104. In the embodiment shown in FIG. 4d, the cup 110 may include a male taper 121 which is received in a corresponding female taper 123 of the proximal end 115 of the humeral stem 114. FIG. 4e shows a bearing 192 of a modular cup 110 that has a concave surface 124 and a female taper 144 adapted to receive a modular glenoid stem 130 or modular humeral stem 136, such as those shown in FIGS. 15 and 16 in connection with the modular adapter 113. The bearing 192 may also be used with the embodiments of FIGS. 13 and 14, as is described below.

Referring to FIGS. 15 and 16, the modular adapter 113 may include a body 150 with a male taper 152 and a female taper 154. The female taper 154 is adapted to receive a glenoid stem 134 for the reverse shoulder arthroplasty and a humeral stem 136 for the traditional shoulder arthroplasty. The male taper 152 is adapted to be received in the female taper 142 of the embodiment of the head 108 shown in FIG. 9b or in the female taper 120 of the embodiment of the head 108 shown in FIG. 9c, for example.

In general, the adapter 112 may be modular, such as the adapter 113 of FIGS. 15 and 16, or a monolithic adapter. The adapter 112 may be a single, one and the same, adapter that can be used selectively in both the traditional and the reverse shoulder arthroplasty, or it can be chosen from a number of available adapters of an assembly of components, such as those shown in FIGS. 3a-3d, depending on which arthroplasty procedure is to be performed. Some of these adapters 112, such as, for example, the adapter shown in FIG. 3c, may be specifically configured for use with reverse arthroplasty, because they incorporate the glenoid stem 134, either modularly or monolithically.

Figure 3A:
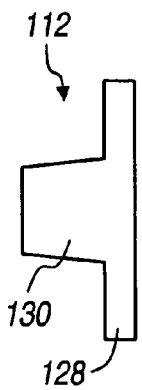
FIGS. 3a-3d are side views of embodiments of an adapter according to the present invention.
Figure 3B:
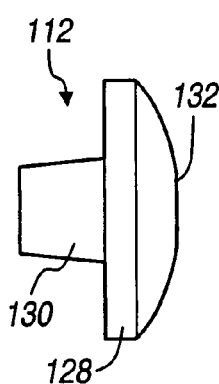
Figure 3C:
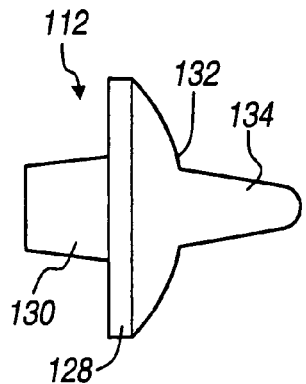
Figure 3D:
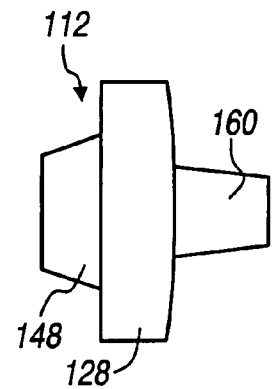

In one embodiment, the adapter 112 may include an adapter tray 128 and an extension or male taper 130 that can be press-fitted into the female taper 120 of the head 108. For the procedure of traditional shoulder arthroplasty, the tray 128 is attached to the proximal end of the humeral stem 114, as shown in FIG. 1. For the procedure of reverse arthroplasty, the tray 128 is attached to the glenoid 104, as shown in FIG. 2. In the embodiments of FIGS. 3a and 3c, the tray 128 may include a curved portion 132 shaped to conform with a portion of the glenoid 104. It may also include the glenoid stem 134, which is inserted into the glenoid 104. The adapter may be attached to the glenoid 104 with fasteners, such as screws.

Referring to the embodiment of FIG. 3a, the tray 128 may also be substantially planar. It will be appreciated, however, that other shapes, in addition to those shown in FIGS. 3a-3d, are possible for the tray 128 depending, for example, on the various ways the tray 128 is be attached to the humerus 102, to the humeral stem 114, or to the glenoid 104. Furthermore, the adapter 112 may be modular, such that the male taper 130, the tray 128 and the glenoid stem 134 are all separate components interconnected though fasteners, such as screws, or other type of connectors, including male-female tapers as illustrated in FIGS. 15 and 16. The adapters 112, 112a shown in FIGS. 3d and 5a include a male taper 148 which can be received in the female taper of 120 of the head 108, 108a, and a male taper 160 which can be received in the female taper 123 of the humeral stem 114.

Figure 5B:
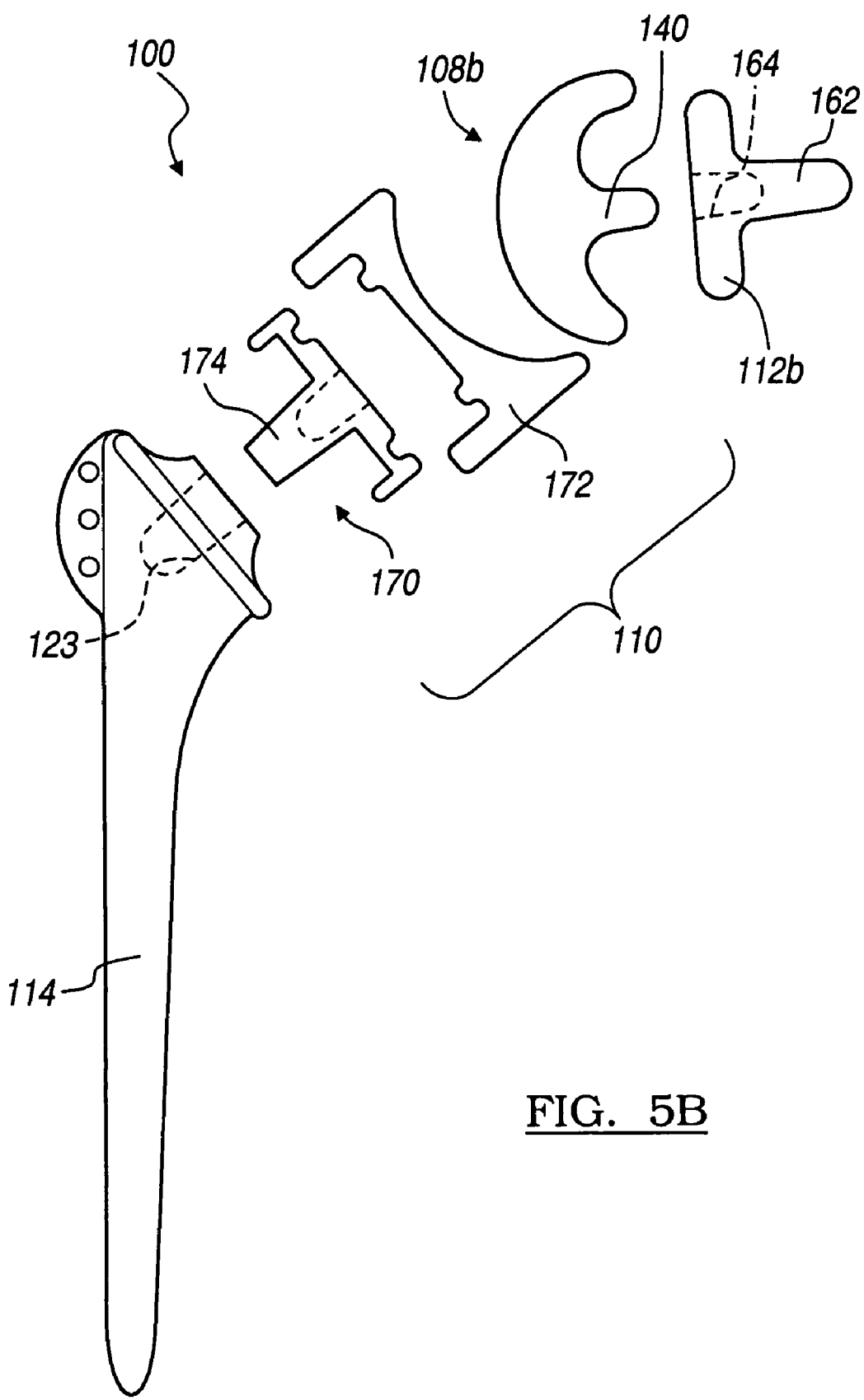
FIG. 5b is an exploded view of an embodiment of an implant assembly according to the invention, shown in a reverse shoulder arthroplasty.
Figures 6A, 6B:
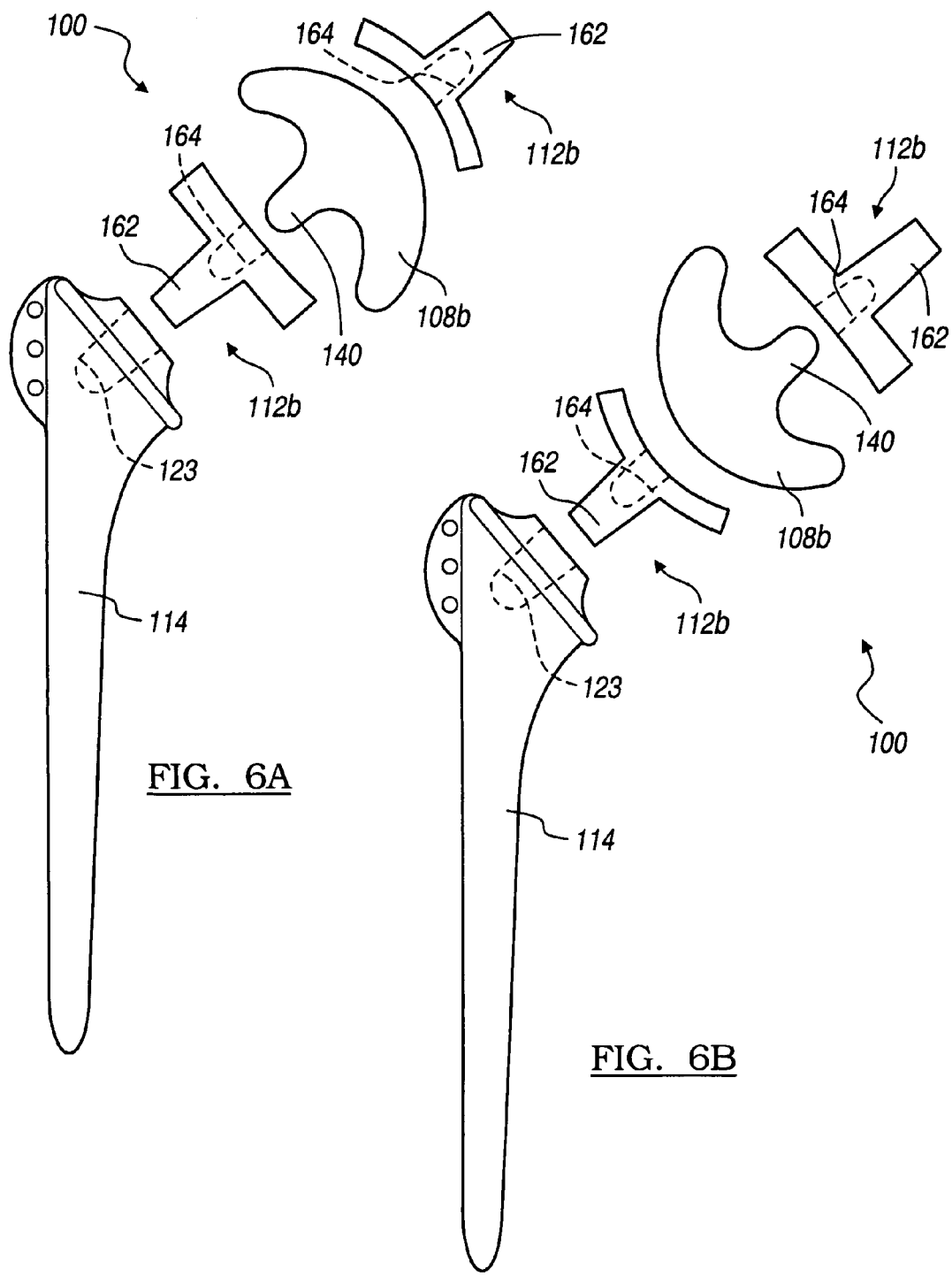
FIG. 6a is an exploded view of an embodiment of an implant assembly according to the invention, shown in a traditional shoulder arthroplasty.
FIG. 6b is an exploded view of an embodiment of an implant assembly according to the invention, shown in a reverse shoulder arthroplasty.
Figure 7:
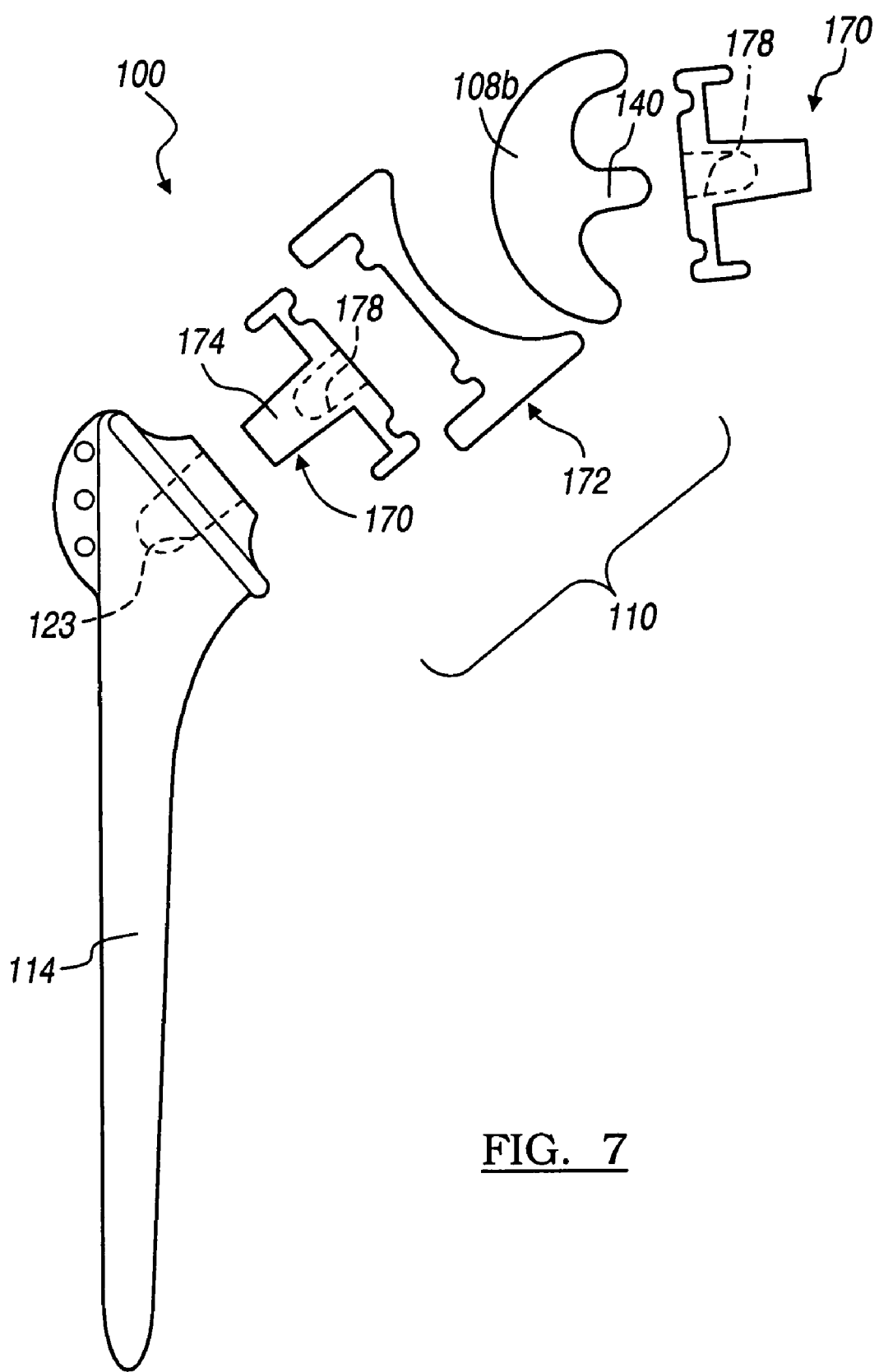
FIG. 7 is an exploded view of an embodiment of an implant assembly according to the invention, shown in a reverse shoulder arthroplasty.
Figure 8:
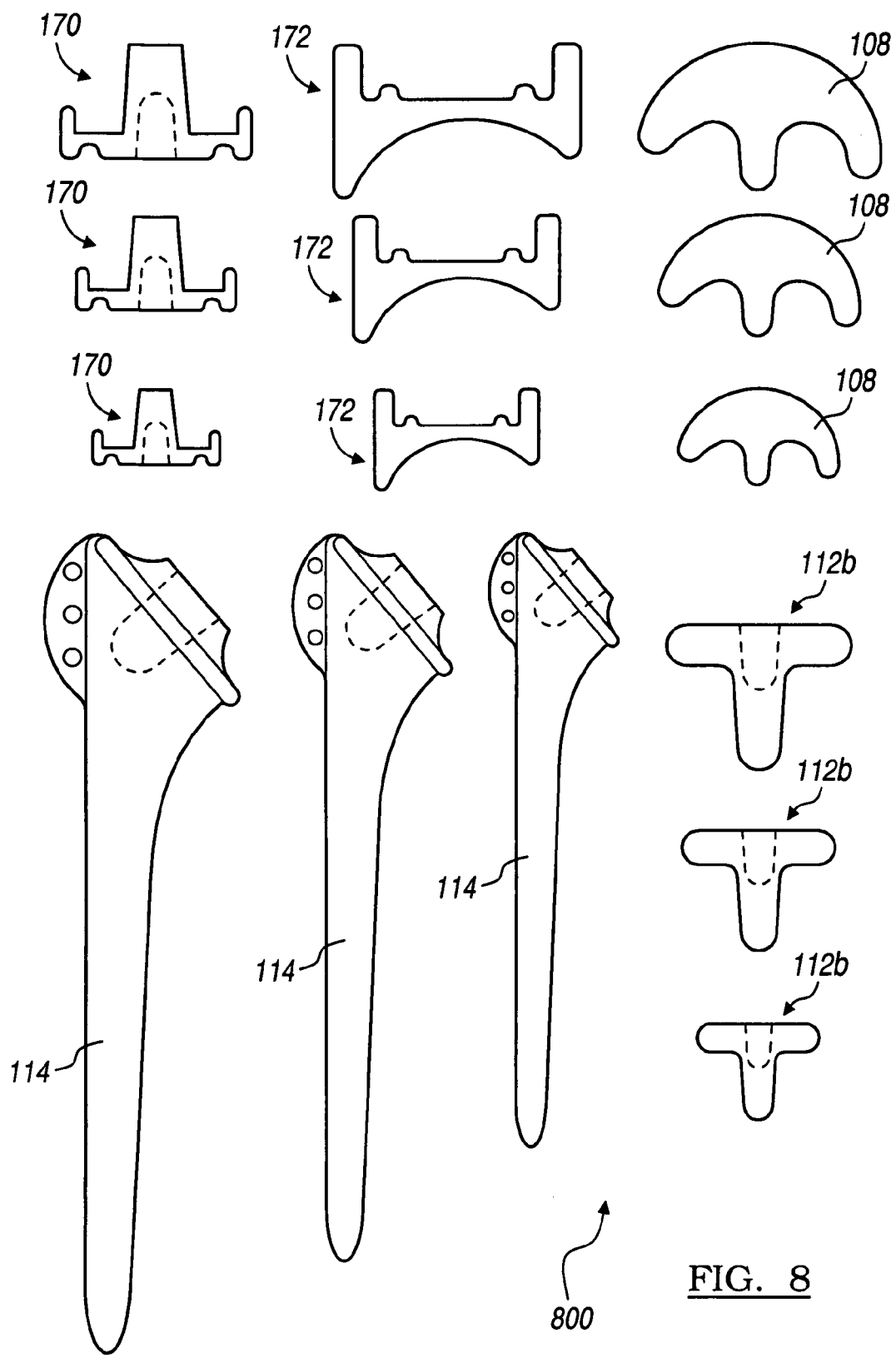
FIG. 8 is an embodiment of a assembly of components for shoulder arthroplasty according to the invention.
Figure 11A:
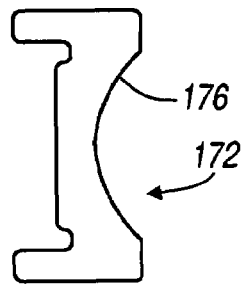
FIGS. 11a-11c are side views of embodiments of head bearings.
Figure 11B:
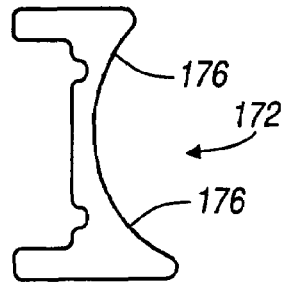
Figure 11C:
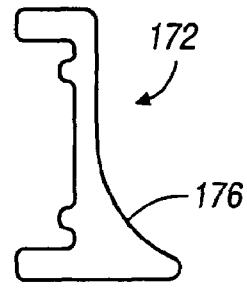

In the embodiments illustrated in FIGS. 5b and 7, the cup 110 may be replaced by a bearing base 170, which is also an adapter, and a bearing 172 that can be fitted to the base 170. The bearing base 170 has a male taper 174 configured to be received in the female taper 123 of the humeral stem 114. Examples of bearings 172 with symmetric or non-symmetric and eccentric bearing surfaces 176 are shown in FIGS. 11a-11c. In the embodiment of FIG. 7, the bearing base 170, includes a female taper 178 adapted to receive the male taper 140 of the head 108b.

Figure 12:
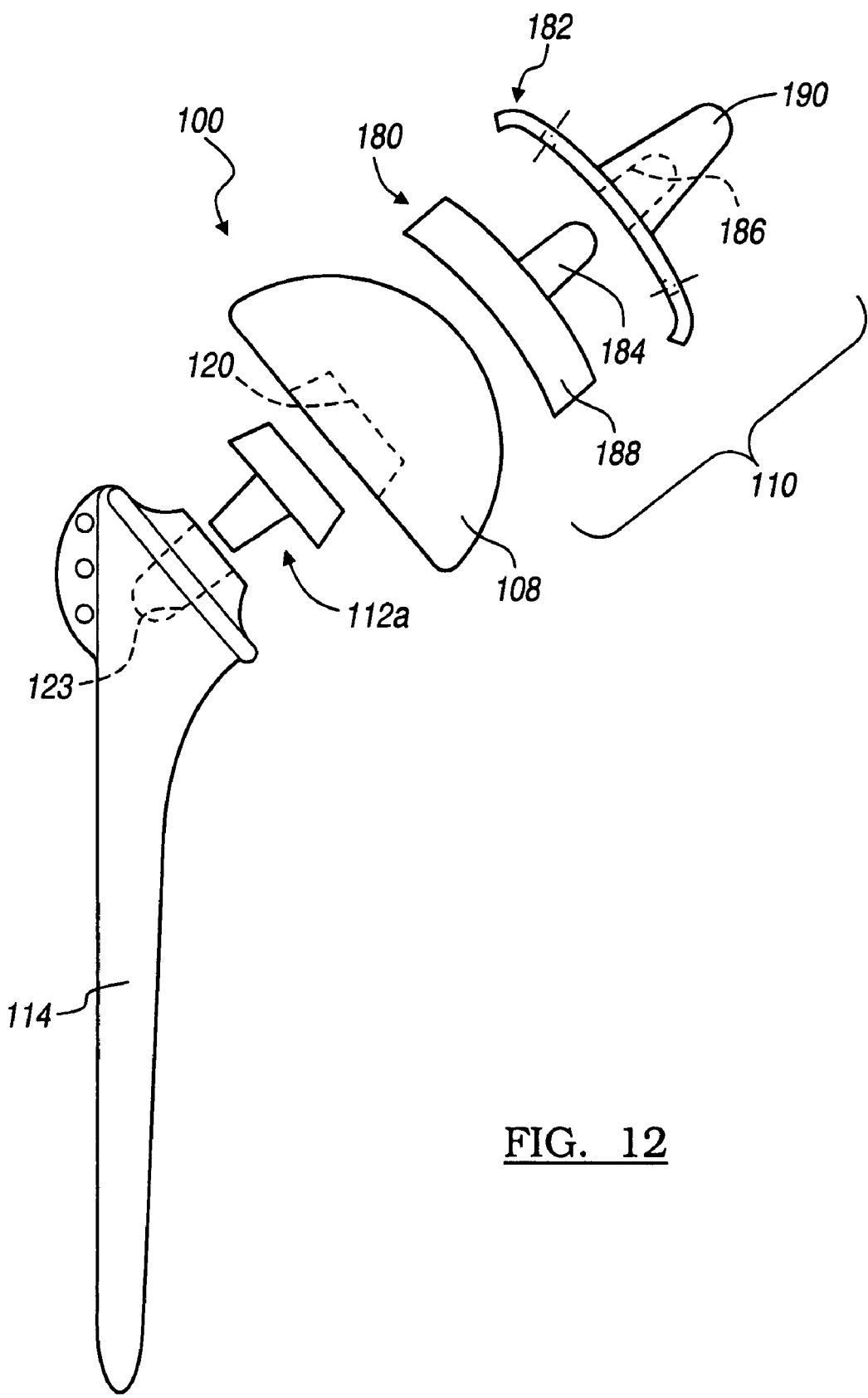
FIG. 12 is an exploded view of an embodiment of an implant assembly according to the invention, shown in a traditional shoulder arthroplasty.

In the embodiment of FIG. 12, the cup 110 may be replaced by a bearing 180 that is fitted in a bearing base 182 with mating male taper 184 and female taper 186, or with a bearing 180 that includes only a liner 188. The bearing base 182 may include a modular or integral glenoid stem 190.

Referring to FIGS. 1 and 2, for example, the implant assembly 100 may be used as follows. The humeral stem 114 is inserted in the resected humerus 102. The adapter 112 is attached to the head 108 by inserting the male taper 130 into the female taper 120. For traditional shoulder arthroplasty, the cup 110 is attached to the glenoid 104, and the adapter 112 is attached to the proximal end 115 of the humeral stem 114, such that the convex surface 116 of head 108 articulates with the concave surface 124 of the cup 110. For reverse shoulder arthroplasty, the cup 110 is attached to the proximal end 115 of the stem humeral 114 and the adapter 112 is attached to the resected glenoid 104 such that the convex surface 116 of head 108 articulates with the concave surface 124 of the cup 110. Although the same adapter 112 can be used for both the traditional and the reverse shoulder arthroplasty procedures, glenoid-specific adapters 112 may be chosen, either as integral components or built from modular parts that include male tapers 130, trays 128 and glenoid stems 134.

It will be appreciated that the individual components of the implant assembly 100 may be made using a variety of materials, including metal and plastic. The head and the stem may be made of metallic material, such as a cobalt chrome alloy, for example. Porous coating may be provided for the proximal end of the stem. The cup may be made of polyethylene or metal or a combination thereof, such as polyethylene bearing or lining and metal base. The adapter can be typically made of metal.

Other exemplary embodiments are illustrated in FIGS. 5a, 5b, 6a, 6b, 7, and 12-14. In FIG. 5a, the male taper 140 of the head 108b can also be inserted directly into the female taper 123 of the humeral stem 123. Alternatively, an adapter 112b having a male taper 162 and a female taper 164 may be provided. The adapter 112b may be also used in the embodiments shown in FIGS. 5b, 6a, and 6b.

Figure 13:
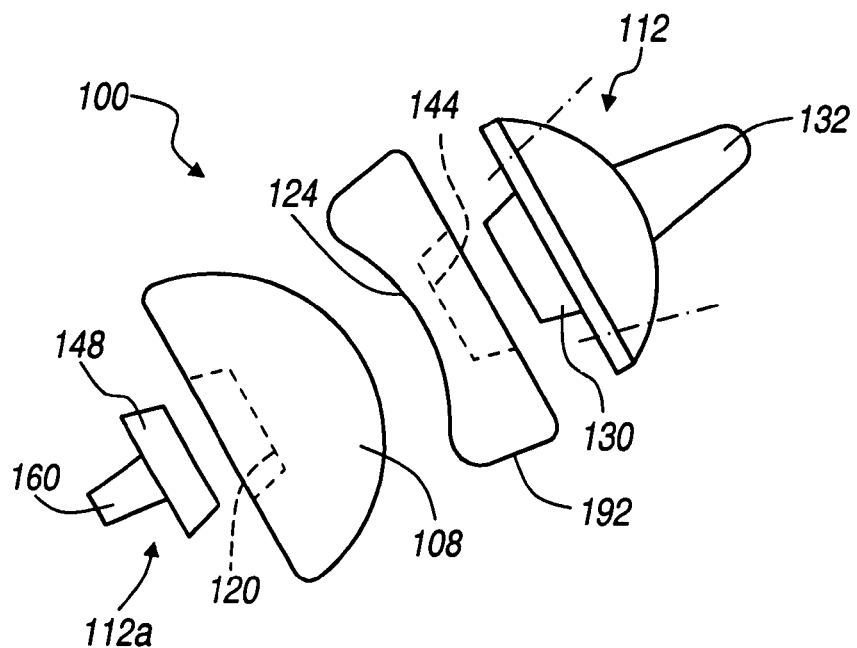
FIG. 13 is an exploded view of an embodiment of an implant assembly according to the invention, shown in a traditional shoulder arthroplasty without a humeral stem.
Figure 14:
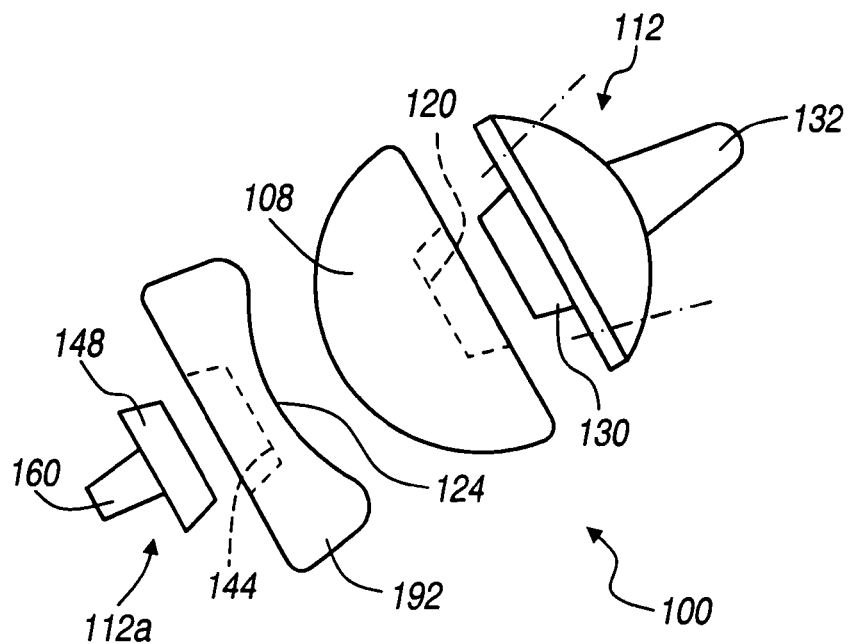
FIG. 14 is an exploded view of an embodiment of an implant assembly according to the invention, shown in a reverse shoulder arthroplasty without a humeral stem.

In the embodiments of FIGS. 13 and 14, the male taper 148 of the adapter 112a can be received in the female taper 120 of the head 108 for the traditional shoulder arthroplasty shown in FIG. 13, and in the female taper 144 of the bearing 192 for the reverse arthroplasty shown in FIG. 14. Similarly, the male taper 130 of the glenoid adapter 112 may be received in the female taper 120 of the head 108 for the reverse shoulder arthroplasty, and in the female taper 144 of the bearing 192 for the traditional shoulder arthroplasty.

While the invention has been described in the specification and illustrated in the drawings with reference to a preferred embodiment, it will be understood by those skilled in the art that various changes may be made and equivalents may be substituted for elements thereof without departing from the scope of the invention as defined in the claims. In addition, many modifications may be made to adapt a particular situation or material to the teachings of the invention without departing from the essential scope thereof. Therefore, it is intended that the invention not be limited to the particular embodiments illustrated by the drawings and described in the specification as the best modes presently contemplated for carrying out this invention, but that the invention will include any embodiments falling within the foregoing description and the appended claims.

What is claimed is:

1. A method for selectively performing reverse and traditional arthroplasty for a shoulder joint that includes a humerus and a glenoid, the method comprising:
providing a head, a cup and a humeral stem;
providing a humeral adapter for attaching the head to the humeral stem in traditional arthroplasty;
providing a glenoid adapter for attaching the head to the glenoid in reverse arthroplasty;
selecting one of the humeral and glenoid adapters; and
performing the corresponding arthroplasty utilizing the head, the cup, the humeral stem and the selected adapter.

2. The method of claim 1, wherein the humeral and glenoid adapters are the same adapter.

3. The method of claim 2, wherein the adapter includes a first male taper selectively attachable to one of the humeral stem and a glenoid stem.

4. The method of claim 3, wherein the adapter includes a second male taper configured to be received in a female taper of the head.

5. The method of claim 1, wherein performing the corresponding arthroplasty includes:
attaching the glenoid adapter to the glenoid;
attaching the glenoid adapter to the head;
attaching the cup to the humeral stem; and
articulating the head with the cup.

6. The method of claim 1, wherein performing the corresponding arthroplasty includes:
attaching the humeral adapter to the humeral stem;
attaching the humeral adapter to the head;
attaching the cup to the glenoid; and
articulating the head with the cup.

7. The method of claim 6, wherein attaching the glenoid adapter to the glenoid includes attaching a glenoid stem to the adapter and implanting the glenoid stem to the glenoid.

* * * * *